United States Patent [19]

Wermuth et al.

[11] 4,038,317

[45] July 26, 1977

[54] O-AMINOALKYL OXIMES

[75] Inventors: Camille Georges Wermuth; Jean Schwartz, both of Strasbourg, France

[73] Assignee: Seperic, Morat, Switzerland

[21] Appl. No.: 656,970

[22] Filed: Feb. 10, 1976

[30] Foreign Application Priority Data

Feb. 12, 1975 United Kingdom ............... 5956/75

[51] Int. Cl.$^2$ .................. C07C 131/00; C07C 131/02; C07C 131/08
[52] U.S. Cl. ........................ 260/566 AE; 260/465 E; 260/501.1; 424/304; 424/316; 424/327
[58] Field of Search ......... 260/566 AE, 501.1, 465 E; 424/304, 316, 327

[56] References Cited

U.S. PATENT DOCUMENTS

| | | | |
|---|---|---|---|
| 3,040,097 | 6/1962 | Bachman et al. | 260/566 AE |
| 3,526,671 | 9/1970 | Judd | 260/566 AE |
| 3,692,835 | 9/1972 | Van Dijk | 260/566 AE |
| 3,903,164 | 9/1975 | Dahlander et al. | 260/566 AE |

OTHER PUBLICATIONS

Morrison et al. "Organic Chemistry" 3rd ed. pp. 562–565, (1973).

*Primary Examiner*—Gerald A. Schwartz
*Attorney, Agent, or Firm*—Young & Thompson

[57] ABSTRACT

The present invention relates to a compound selected from the group consisting of compounds of formula:

$$R^1_{\phantom{1}}\!\!\!\diagdown\!\!\!\!\!\phantom{X}\!\!\!\!\!\phantom{X}\!\!\!\!\!\phantom{X}\!\!\!\!\!\phantom{X}\!\!\!\!\!\phantom{X}$$

$$R^1R^2C{=}N{-}O{-}CH_2{-}CH(OH){-}CH_2{-}NH{-}R^3$$

in which:
   $R^1$ is selected from the group consisting of phenyl, phenyl substituted by a radical selected from $C_1$-$C_4$ alkyl, $C_1$-$C_4$ alkoxy, halogen, nitro, amino and cyano, and naphthyl,
   $R^2$ is selected from the group consisting of hydrogen, $C_1$-$C_4$ alkyl, and phenyl, or, together with the carbon atom to which they are attached, $R^1$ and $R^2$ form a polycyclic ring selected from the rings derived from fluorene, xanthene, indane, tetrahydronaphthalene, dihydrodibenzocycloheptene and dibenzocycloheptene,
   $R^3$ is selected from the group consisting of isopropyl and tert. butyl, and a pharmaceutically acceptable acid addition salt thereof.

Such a compound is useful as anti-hypertensive drug.

3 Claims, No Drawings

O-AMINOALKYL OXIMES

This invention relates to new oximes, a process for their preparation and their therapeutic applications.

This invention relates to a compound selected from the group consisting of compounds for formula:

$$\begin{array}{c} R^1 \\ \phantom{R}\diagdown \\ \phantom{RR}C=N-O-\underset{\underset{H}{|}}{\overset{\overset{H}{|}}{C}}-\underset{\underset{OH}{|}}{\overset{\overset{H}{|}}{C}}-\underset{\underset{H}{|}}{\overset{\overset{H}{|}}{C}}-N-R^3 \\ R^2\diagup \end{array} \quad (I)$$

in which:
- $R^1$ is selected from the group consisting of phenyl, phenyl substituted by a radial selec ed from $C_1$-$C_4$ alkyl, $C_1$-$C_4$ alkoxy, halogen, nitro, amino and cyano, and naphthyl,
- $R^2$ is selected from the group consisting of hydrogen, $C_1$-$C_4$ alkyl, and phenyl, or together with the carbon atom to which they are attached, $R^1$ and $R^2$ form a polycyclic ring, selected from the rings derived from fluorene, xanthene, indane, tetrahydronaphthalene, dihydrodibenzocycloheptene and dibenzocycloheptene,
- $R^3$ is selected from the group consisting of isopropyl and tert.butyl, and a pharmaceutically acceptable acid addition salt thereof.

The compounds (I) may be prepared by a process illustrated by the following scheme:

(II) $\begin{array}{c} R^1 \phantom{xx} R^2 \\ \diagdown\phantom{x}\diagup \\ C \\ \parallel \\ N \\ | \\ O \\ | \\ H \end{array}$ + Cl—CH$_2$—CH———CH$_2$ (III)
$\phantom{xxxxxxxxxxxxxxxxxxx}\diagdown\phantom{x}\diagup$
$\phantom{xxxxxxxxxxxxxxxxxxxxx}$O $\downarrow$ $\begin{array}{c} R^1 \phantom{xx} R^2 \\ \diagdown\phantom{x}\diagup \\ C \\ \parallel \\ N \\ | \\ O-CH_2-CH———CH_2 \\ \phantom{xxxxxxxx}\diagdown\phantom{x}\diagup \\ \phantom{xxxxxxxxxxx}O \end{array}$ + R$^3$NH$_2$ $\longrightarrow$ (I)
(IV) $\phantom{xxxxxxxxx}$(V)

In a first step, this process comprises condensing an oxime of the formula (II) in which $R^1$ and $R^2$ have the aforesaid meanings with the epichlorohydrin of the formula (III).

This condensation may be effected by treating the oxime with sodium methoxide or ethoxide within methanol or ethanol. After complete evaporation of the solvent, the sodio oxime derivative is dissolved in dimethylformamide (DMF) to which is gradually added the epichlorohydrin in DMF solution.

An epoxide having the formula (IV) may thus be obtained.

In a second step, the epoxide of the formula (IV) is reacted with a primary amine of the formula (V) in which $R^3$ has the aforesaid meaning. This reaction is advantageously conducted within benzene, at a temperature of about 90° C.

After evaporation of the solvent, the resulting product of the formula (I) may be dissolved in a suitable solvent, if desired, to convert the compounds (I) to salts with pharmaceutically acceptable acids. The conventional procedures well known in organic chemistry are used to obtain, by recrystallization, evaporation, extraction or any other means a product of the formula (I) of adequate purity.

The following examples are given to illustrate the invention without, however, limiting same.

EXAMPLE 1

Preparation of 9-(3-tert.butylamino-2-hydroxypropoxy)imino-fluorene hydrochloride $\begin{array}{c} R^1 \\ \diagdown \\ \phantom{x}C= \\ \diagup \\ R^2 \end{array}$ = fluorenylidene; $R_3$ = tert.butyl.

Empirical formula: $C_{20}H_{25}O_2N_2Cl$

1. Preparation of 9-(2,3-epoxy-propoxy)-imino-fluorene 10 g Fluorenone oxime are refluxed during one hour in 130 ml methanol containing 1.18 g sodium.

The methanol is completely evaporated off and the residue is taken up into 80 ml dimethyl formamide (DMF). The resulting material is transferred into a dropping funnel and 20 ml DMF containing 4.75 g epichlorohydrin, heated to 50° C, are gradually added.

A sodium chloride precipitate is formed. The reaction mixture is stirred during one hour, until the reaction is complete. It is then poured over 500 ml water and extracted with 3 × 100 ml chloroform. The organic phase is washed twice with water. It is then dried with magnesium sulfate and evaporated to dryness, to given an oil which crystallizes as yellow crystals from hexane.

2. Condensation with the primary amine

The resulting epoxide is dissolved in 20 ml benzene, in a 100 ml ampode containing 14 g tert.butylamine. The resulting mixture is heated overnight in an oven at 90° C.

The solvent and excess reagent are then evaporated; the resulting oil is dissolved in isopropanol and an equimolar solution of oxalic acid in acetone is added thereto.

The oxalate crystallizes on addition of ether. After filtration and repeated washing with ether, the oxalate is suspended in water made alkaline with potassium hydrogen carbonate and extracted with chloroform.

The organic phase is evaporated and the hydrochloride is produced by treatment of the product with hydrochloric acid in isopropanol solution, to give 6.3 g of the oxime of the formula (I). The melting point is 149°–150° C.

| Analysis: | C% | H% | N% |
| --- | --- | --- | --- |
| Calculated: | 66.56 | 6.98 | 7.76 |
| Found: | 66.48 | 7.00 | 7.75 |

EXAMPLE 2

Preparation of 4-chloro-acetophenone-0-(3-tert.butylamino-2-hydroxy-propyl)oxime hydrochloride $R^1$ = 4-chlorophenyl; $R^2$ = methyl; $R^3$ = tert.butyl
Empirical formula: $C_{15}H_{24}N_2O_2Cl_2$ 1. Preparation of 4-chloro-acetophenone-0-(2,3-epoxy-propyl)-oxime 10 g of para-chloro-acetophenone oxime are refluxed during one hour in 100 ml methanol containing 1.36 g sodium.

The methanol is completely evaporated off and the residue is taken up into 50 ml DMF. The material is transferred into a dropping funnel and 15 ml DMF containing 6 g epichlorohydrin, heated to 50° C, are added thereto, dropwise.

After stirring during one hour, 500 ml water is added and the reaction mixture is then extracted with 3 × 100 ml chloroform. The organic phase is washed twice with water. It is then dried with magnesium sulfate and evaporated to dryness.

2. Condensation with the primary amine

The resulting crude epoxide is dissolved in 20 ml benzene, in the presence of excess isopropylamine in a 100 ml ampoule. This is a mixed, after which the ampoule is sealed and heated to 100° C during 12 hours.

The solvent and excess reagent are then evaporated off. The resulting oil is dissolved in isopropanol and the hydrochloride of the desired oxime is precipitated by bubbling hydrochloride acid through the isopropanol solution.

The material is recrystallized from isopropanol-ether (1:1), to give 8.2 g of product of the formula (I). M.P. = 133°-134° C.

| Analysis:   | C%    | H%   | N%   |
|-------------|-------|------|------|
| Calculated: | 54.05 | 7.21 | 8.36 |
| Found:      | 54.13 | 7.20 | 8.43 |

EXAMPLE 3

Preparation of 2-naphthalene carbaldehyde-0-(3-isopropylamino-2-hydroxy-propyl)-oxime hydrochloride $R^1$ = 2-naphthyl; $R^2$ = H; $R^3$ = isopropyl.
Empirical formula: $C_{19}H_{23}N_2OCl$ 1. Preparation of 2-naphthalene carbaldehyde-0-(2,3-epoxypropyl)oxime 5 g 2-naphthaldehyde oxime are refluxed during one hour in 50 ml methanol, in the presence of 0.675 g sodium.

The solvent is evaporated off and the residue is taken up into 25 ml DMF. It is then transferred into a dropping funnel and 10 ml DMF containing 2.7 g epichlorohydrin, heated to 50° C, are added thereto portionwise.

The material is stirred during one hour, until the reaction is complete. Water (50 ml) is added and the reaction mixture is extracted with 3 × 100 ml chloroform. The organic phase is washed twice with water, dried with magnesium sulfate and evaporated to dryness.

2. Condensation with the primary amine

The resulting crude epoxide is dissolved in 20 ml benzene, in the presence of excess isopropylamine, in a 100 ml ampoule. After mixing, the ampoule is sealed and heated to 100° C during 2 hours.

The solvent and excess reagent are evaporated off. The resulting material is dissolved in isopropanol and the hydrochloride is precipitated out by bubbling hydrochloric acid through the solution.

Recrystallization from isopropanol-ether (1:1) gives 6.5 g of oxime of the formula (I) (as the hydrochloride). Melting point is 189°-190° C.

| Analysis:   | C%    | H%   | N%   |
|-------------|-------|------|------|
| Calculated: | 63.22 | 7.18 | 8.68 |
| Found:      | 63.29 | 7.32 | 8.87 |

EXAMPLE 4

Preparation of benzophenone-0-(3-tert.butylamino-2-hydroxy-propyl)-oxime hydrochloride $R^1$ = $R^2$ = phenyl; $R^3$ = tert.butyl.
Empirical formula: $C_{20}H_{27}O_2N_2Cl$ 1. Preparation of benzophenone-0-(2,3-epoxypropyl)-oxime 10 g of benzophenone oxime are refluxed during one hour in 100 ml methanol containing 1.17 g sodium.

The methanol is completely evaporated off and the residue is taken up into 80 ml DMF. The material is transferred into a dropping funnel and 20 ml DMF containing 4.7 g epichlorohydrin, heated to 50° C, are added thereto.

The reaction mixture is stirred during one hour, until the reaction is complete. Water (500 ml) is then added thereto and the material is extracted with 3 × 100 ml chloroform.

The organic phase is washed twice with water. It is then dried with magnesium sulfate and evaporated to dryness.

2. Condensation with the primary amine

The resulting crude epoxide is then dissolved in 20 ml benzene, in the presence of excess tert.butylamine, in a 100 ml ampoule. After mixing, the ampoule is sealed and heated to 90° C during 12 hours.

The solvent and excess reagent are then evaporated off. The resulting product is dissolved in isopropanol. The oxime hydrochloride precipitates out by bubbling hydrochloric acid therethrough.

The product is recrystallized from isopropanol-ether (1:1), to give 9.4 g of the hydrochloride of the oxime of formula (I). M.p. = 151°-152° C.

| Analysis:   | C%    | H%   | N%   |
|-------------|-------|------|------|
| Calculated: | 66.20 | 7.50 | 7.72 |
| Found:      | 66.4  | 7.61 | 7.93 |

The physical characteristics of the compounds thus prepared, together with those of other compounds according to this invention prepared in a similar manner are tabulated in following Table I.

It should be noted that all melting points given in the Table were measured with a Maquenne block.

TABLE I

| Example | $R^1$ or 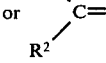 | $R^2$ | $R^3$ | M.p. ±2° C | M.W. | Salt |
|---------|------------|--------|------------|------|-------|---------------|
| 1 | Fluorenylidene | | Tert.butyl | 150 | 360.9 | Hydrochloride |
| 2 | p-Cl-phenyl | Methyl | Tert.butyl | 134 | 335.3 | " |

TABLE I-continued

| Example | R¹ (R¹\C= or R²/) | R² | R³ | M.p. ±2° C | M.W. | Salt |
|---|---|---|---|---|---|---|
| 3 | 2-Naphthyl | H | Isopropyl | 190 | 322.8 | " |
| 4 | Phenyl | Phenyl | Tert.butyl | 152 | 362.9 | " |
| 5 | 10,11-dihydro-5H-dibenzo(a-d)cyclohepten-5-ylidene | | Isopropyl | 198 | 374.9 | " |
| 6 | " | | Tert.butyl | 194 | 388.9 | " |
| 7 | 5H-dibenzo(a-d)cyclohepten-5-ylidene | | Tert.butyl | 230 | 386.9 | " |
| 8 | " | | Isopropyl | 214 | 372.9 | " |
| 9 | Fluorenylidene | | Isopropyl | 153 | 346.8 | " |
| 10 | Xanthenylidene | | Isopropyl | 157 | 362.9 | " |
| 11 | " | | Tert.butyl | 208 | 376.9 | " |
| 12 | Indan-5-ylidene | | Isopropyl | 136 | 296.8 | " |
| 13 | Phenyl | Methyl | Isopropyl | 128 | 286.8 | Hydrochloride |
| 14 | Phenyl | Phenyl | Isopropyl | 188 | 348.9 | " |
| 15 | 1,2,3,4-tetrahydronaphthalen-1-ylidene | | Isopropyl | 110 | 312.8 | " |
| 16 | Phenyl | H | Isopropyl | 162 | 272.8 | " |
| 17 | p-Tolyl | Methyl | Tert.butyl | 122 | 394.5 | Maleate |
| 18 | 1,2,3,4-tetrahydronaphthalen-1-ylidene | | Tert.butyl | 149 | 406.6 | Maleate |
| 19 | Phenyl | H | Tert.butyl | 198 | 286.8 | Hydrochloride |
| 20 | o-chlorophenyl | Methyl | Tert.butyl | 127 | 414.9 | Maleate |
| 21 | Phenyl | Methyl | Tert.butyl | 124 | 300.8 | Hydrochloride |
| 22 | p-Methoxyphenyl | Methyl | Tert.butyl | 141 | 330.8 | " |
| 23 | p-Nitrophenyl | Methyl | Tert.butyl | 219 | 345.8 | " |
| 24 | o-Tolyl | Methyl | Tert.butyl | 157 | 394.5 | Maleate |
| 25 | p-Bromophenyl | Methyl | Tert.butyl | 105 | 458.3 | Maleate |
| 26 | m-Tolyl | Methyl | Tert.butyl | 117 | 394.5 | Maleate |
| 27 | p-Aminophenyl | Methyl | Tert.butyl | 140 | 378.4 | Oxalate |
| 28 | 2-Naphthyl | H | Tert.butyl | 114 | 416.5 | Maleate |
| 29 | p-Tolyl | Methyl | Tert.butyl | 134 | 408.5 | Maleate |
| 30 | p-Cumenyl | Methyl | Tert.butyl | 134 | 422.5 | Maleate |
| 31 | p-Cyanophenyl | Methyl | Tert.butyl | 220 | 335.4 | Oxalate |

The compounds of this invention possess pharmacologic activity, and particularly a beta-blocking activity. They behave as competitive type antagonists with respect to isoprenaline.

This competitive type antagonism was demonstrated in vitro:
- on the isolated auricle of guinea-pigs: the compounds of this invention inhibit the positive inotropic and positive chronotropic effects of isoprenaline;
- on the isolated trachea of guinea-pigs: they inhibit the relaxation due to the action of this same isoprenaline.

The following Table gives the PA$_2$ determined with respect to this agonist (PA$_2$ is the cologarithm of the antagonist concentration in the presence of which it is required to use twice as much agonist than in its absence to obtain the same effect; vide, on the subject; Calcul des PA$_2$, Fiche Technique n° 16, J. Pharmacol. Paris, 1971, 2, 3, 373–380).

| Example | Isolated auricle of guinea-pig PA$_2$ Chronotropic effect | Isolated auricle of guinea-pig PA$_2$ Inotropic effect | Isolated trachea of guinea-pig PA$_2$ Relaxation |
|---|---|---|---|
| 2 | 7.58 | 7.43 | 6.61 |
| 3 | 6.53 | 6.94 | 9.37 |
| 4 | 6.79 | 6.37 | 7.96 |
| 9 | 7.39 | 7.10 | 6.78 |
| 10 | 7.10 | 6.66 | 6.81 |
| 12 | 6.44 | 6.29 | — |
| 13 | 6.64 | 6.73 | 7.54 |
| 14 | 6.79 | 6.72 | 7.49 |
| 15 | 6.17 | 6.12 | 7.90 |
| 16 | 5.52 | 5.62 | 6.89 |
| 17 | 7.83 | 7.86 | 7.89 |
| 18 | 7.15 | 7.54 | 9.20 |
| 19 | 6.26 | 6.57 | 6.23 |
| 20 | 8.34 | 8.37 | 7.86 |
| 21 | 6.70 | 6.93 | 7.62 |
| 22 | 7.85 | 7.94 | 8.74 |
| 23 | 7.46 | 7.60 | 7.54 |
| 24 | 6.66 | 6.69 | 7.90 |
| 25 | 7.58 | 7.90 | 8.51 |
| 26 | 8.11 | 8.10 | 8.30 |
| 27 | 7.64 | 7.84 | 7.10 |
| 28 | 7.45 | 7.49 | 7.37 |
| 29 | 7.19 | 7.19 | 6.97 |
| 31 | 6.92 | 6.91 | 6.99 |

This beta-blocking activity is again apparent in vivo. The compounds inhibit, in particular, the action of isoprenaline on some cardiac parameters in anesthetized dog.

The following Table sets forth the dosages which inhibit 50% of the effect of 0.02 micromole/kg of isoprenaline on blood pressure, on cardiac rhythm and on the contractile strength of the heart.

| 50% INHIBITING DOSAGE (MICROMOLES/KG) of the ACTION of ISOPRENALINE | | | |
|---|---|---|---|
| Example | Blood pressure | Rhythm | Contractile strength |
| 1 | 0.2 | 3 | 3 |
| 2 | 1 | > 10 | 10 |
| 9 | 1.3 | > 17 | > 17 |
| 18 | 0.05 | > 1 | > 1 |
| 20 | 0.07 | 1 | 0.7 |
| 23 | 0.10 | 3 | 3 |

The compounds of this invention are therapeutically useful for the treatment of cardiovascular conditions, as anti-hypertensive drugs.

Having now described our invention what we claim as new and desire to secure by Letters Patent is:

1. A compound selected from the group consisting of compounds of formula:

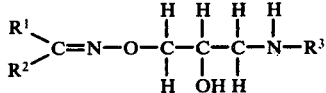

(I)

in which:
R¹ is selected from the group consisting of phenyl phenyl substituted by a radical selected from $C_1$-$C_4$ alkyl, $C_1$-$C_4$ alkoxy, halogen, nitro, amino and cyano, and naphthyl,
R² is selected from the group consisting of hydrogen, $C_1$-$C_4$ alkyl, and phenyl, or together with the carbon atom to which they are attached, R¹ and R² form a polycyclic ring, selected from the rings derived from fluorene, xanthene, indane, tetrahydronaphthalene, dihydrodibenzocycloheptene and dibenzocycloheptene,
R³ is selected from the group consisting of isopropyl and tert.butyl, and a pharmaceutically acceptable acid addition salt thereof.

2. A compound selected from the group consisting of a compound of the formula

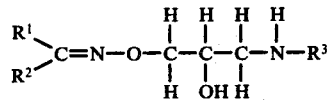

in which:
R¹ is selected from the group consisting of phenyl, and phenyl substituted by a radical selected from $C_1$-$C_4$ alkyl, $C_1$-$C_4$ alkoxy, halogen, nitro, amino and cyano,
R² is selected from the group consisting of hydrogen, $C_1$-$C_4$ alkyl, and phenyl,
R³ is selected from the group consisting of isopropyl and tert.butyl,
and a pharmaceutically acceptable acid addition salt thereof.

3. 2-Chloro-acetophenone-0-(3-tert.butylamino-2-hydroxy propyl) oxime and a pharmaceutically acceptable acid addition salt thereof.

* * * * *